(12) United States Patent
Hong et al.

(10) Patent No.: US 7,320,804 B2
(45) Date of Patent: Jan. 22, 2008

(54) COUGH DEPRESSANT COMPOSITION CONTAINING IRON FOR ANGIOTENSIN-CONVERTING ENZYME INHIBITOR INDUCING COUGH

(75) Inventors: Kyung-Pyo Hong, Seoul (KR); Seung-Woo Park, Seoul (KR); Sang-Chol Lee, Seongnam (KR)

(73) Assignee: Samsung Life Public Welfare Foundation Samsund Medical Center, Seoul (KR)

( * ) Notice: Subject to any disclaimer, the term of this patent is extended or adjusted under 35 U.S.C. 154(b) by 0 days.

(21) Appl. No.: 11/289,005

(22) Filed: Nov. 29, 2005

(65) Prior Publication Data

US 2006/0073215 A1  Apr. 6, 2006

Related U.S. Application Data

(63) Continuation of application No. 10/380,567, filed as application No. PCT/KR01/01542 on Sep. 13, 2001, now abandoned.

(30) Foreign Application Priority Data

Sep. 14, 2000  (KR) .................. 10-2000-0054012

(51) Int. Cl.
*A01N 59/16* (2006.01)
(52) U.S. Cl. .................. 424/646; 424/647; 424/648
(58) Field of Classification Search .................. None
See application file for complete search history.

(56) References Cited

U.S. PATENT DOCUMENTS

| | | |
|---|---|---|
| 4,582,709 A | 4/1986 | Peters et al. |
| 4,994,283 A | 2/1991 | Mehansho et al. |
| 5,122,369 A | 6/1992 | Dye |
| 6,086,919 A | 7/2000 | Bauer et al. |
| 6,420,426 B1 | 7/2002 | Van Zandt |
| 6,569,456 B2 | 5/2003 | Faour et al. |

FOREIGN PATENT DOCUMENTS

WO  WO 96/07400  *  3/1996

OTHER PUBLICATIONS

Merck & Co., "Prinivil", issued Nov. 1995, retrieved from internet Jun. 8, 2005.

Lee et al., "Iron supplementation cough associated with ACE inhibitors", Hypertension, 2001, p. 166, Abstract.
Windholz, et al., eds., "The Merck Index" 9th ed., 1984, p. 735.
Alyn H. Morice, et al., *Angiotensin-Converting Enzyme and the Cough Reflex*; The Lancet, Nov. 1987.
Nigel L. Gilchrist, et al.; *Effect of Sulindac on Angiotensin Converting Enzyme Inhibitor-Induced Cough: Randomised Placebo-Controlled Double-Blind Cross-Over Study*; Journal of Human Hypertension, 1989.
Alfonso R. Gennaro, et al.; *Remington's Pharmaceutical Sciences*; 18th Edition, 1990.
James L. Sebastian, et al.; *Prevalence in an Outpatient Medical Clinic Population*; Angiotensin-Converting Enzyme Inhibitors and Cough; CHEST/99/1/Jan. 1991.
Zafar H. Israili, et al.; *Cough and Angioneurotic Edema Associated with Angiotensin-Converting Enzyme Inhibitor Therapy*; Annals of Internal Medicine, vol. 117, No. 3, Aug. 1992.
Steven R. Simon, et al.; *Cough and ACE Inhibitors*; Arch Intern Med, vol. 152, Aug. 1992.
Günter Weiss, et al.; *Iron Regulates Nitric Oxide Synthase Activity by Controlling Nuclear Transcription*; J. Exp. Med., vol. 180, Sep. 1994.
Alyson J. Fox, et al.; *Bradykinin-Evoked Sensitization of Airway Sensory Nerves: A Mechanism for ACE-Inhibitor Cough*; Nature Medicine, vol. 2, No. 7, Jul. 1996.
Tod A. Flak, et al.; *Autotoxicity of Nitric Oxide in Airway Disease*; Am. J Respir. Crit. Care Med., vol. 154, 1996.
Wolfgang Linz, et al.; *Interactions Among ACE, Kinins and NO*; Cardiovascular Research 43, 1999.
Jasek W., *Austria Codex Fachinformation 1999/2000*, Österreichische Apotheker-Verlagsgesellschaft mbH, Wien 1999, ISBN 3 85200 131 5, pp. 1577-1579.
Sang-Chol Lee, et al.; *Iron Supplementation Inhibits Cough Associated With ACE Inhibitors*; Hypertension; Aug. 2001.
Merck & Co., Inc.; *Prinivil*, Available at <http:/www.druginfonet.com/prinivil.htm>, Visited on Dec. 11, 2001.
Luque et al., "Treatment of ACE Inhibitor-Induced Cough," *Pharmacotherapy*, vol. 19, No. 7, 1999, pp. 804-810.

* cited by examiner

*Primary Examiner*—Michael P. Woodward
*Assistant Examiner*—Eric E. Silverman
(74) *Attorney, Agent, or Firm*—Alston & Bird LLP

(57) ABSTRACT

The present invention relates to a cough depressant composition containing iron for angiotensin-converting enzyme inhibitor inducing cough. The cough depressant composition of the present invention comprises 0.01-100% by weight of $Fe^{2+}$(ferrous) or $Fe^{3+}$(ferric). Furthermore, the cough depressant composition of the present invention can comprise an angiotensin-converting enzyme inhibitor. The cough depressant composition of the present invention relieves the pain of the patient by reducing continuous dry cough.

4 Claims, 1 Drawing Sheet

COUGH DEPRESSANT COMPOSITION CONTAINING IRON FOR ANGIOTENSIN-CONVERTING ENZYME INHIBITOR INDUCING COUGH

CROSS REFERENCE TO RELATED APPLICATIONS

This application is a continuation of application Ser. No. 10/380,567 filed Mar. 13, 2003, now abandoned which is a national phase of PCT/KR01/01542 filed Sep. 13, 2001, which claims priority from Korean Application No. 2000-54012, filed Sep. 14, 2000, which is hereby incorporated by reference in its entirety.

BACKGROUND OF THE INVENTION

The present invention relates to a cough depressant composition containing iron for inhibiting a dry cough, more specifically a cough depressant composition containing iron to treat a dry cough shown in patients who take an angiotensin-converting enzyme inhibitor.

DESCRIPTION OF THE RELATED ART

Angiotensin is a material causing blood vessel contraction and blood pressure elevation in the body and is synthesized from angiotensinogen. Angiotensinogen converts to angiotensin I by renin that is synthesized in the kidney, angiotensin I converts to angiotensin II by an angiotensin converting enzyme (ACE) and angiotensin II has a very strong blood vessel contraction effect so that it elevates blood pressure. Angiotensin II maintains high blood vessel resistance in essential hypertension as well as hypertension accompanying high blood serum renin activity shown in renal artery stenosis, partial endogenous kidney diseases, and malignant hypertension. Thus, in order to treat hypertension, angiotensin-converting-enzyme inhibitor ('ACEI') is used as a medication. The ACEIs are widely used for the treatment of hypertension and after-treatment of congestive heart failure and myocardial infarction.

However, ACEI use is limited due to its various side effects, of which the most troublesome and frequent is persistent dry cough (Sebastian J L, McKinney W P, Kaufman J, Young M J. Angiotensin-converting enzyme inhibitors and cough. Prevalence in an outpatient medical clinic population. Chest 1991; 99:36-9; Israili Z H, Hall W D. Cough and angioneurotic edema associated with angiotensin-converting enzyme inhibitor therapy. Ann Intern Med 1992; 117:234-42; Simon S R, Black H R, Moser M, Berland W E. Cough and ACE inhibitors. Arch Intern Med 1992; 152:1698-700). Dry cough has been reported to occur in 5 to 25% of patients that are subject to ACEI use and some of them have severe dry cough so that they stop taking the ACEIs (Sebastian J L, McKinney W P, Kaufman J, Young M J. Angiotensin-converting enzyme inhibitors and cough. Prevalence in an outpatient medical clinic population. Chest 1991; 99:36-9).

Although mechanisms involving this side effect have not yet been fully elucidated, there have been observations and trials reporting that increments of prostaglandin synthesis or bradykinin accumulation associated with ACEI use is responsible for this effect (Morice A H, Lowry R, Brown M J, Higenbottam T. Angiotensin-converting enzyme and the cough reflex. Lancet 1987; 2:1116-8 Gilchrist N L, Richards A M, March M, Nicholls M G. Effect of sulindac on angiotensin-converting enzyme inhibitor-induced cough: randomized placebo-controlled double-blind cross-over study. J Hum Hypertens 1989; 3:451-5; Fox A J. Lalloo U G, Belvisi M G, Bernareggi M, Chung K F, Barnes P J. Bradykinin-evoked sensitization of airway sensory nerves: a mechanism for ACE-inhibitor cough. Nat Med 1996; 2:814-7). However, controlled trials of ACEI-induced cough suppression using prostaglandin or bradykinin antagonists have been proven to be inconclusive and there is no definite way to inhibit the dry cough caused by angiotensin to date.

Meanwhile, ACEI is known to cause an increase in nitric oxide (NO) generation (Linz W, Wohlfart P, Schoelkens B A, Malinski T, Wiemer G. Interaction among ACE, kinins, and NO. Cardiovasc Res 1999; 43:549-61). Nitric oxide is known to relax on the bronchial smooth muscle cells, but also has inflammatory effects on the bronchial epithelial cells (Flak T A, Goldman W E. Autotoxicity of nitric oxide in airway disease. Am J Respir Crit Care Med 1996; 154(4 pt 2):202-6). Nitric oxide is synthesized by a nitrogen oxide synthase(NOS) and it was reported that the nitric oxide synthase can be deactivated by adding iron (Weiss G, Werner-Felmayer G, Werner E R, Gruenewald K, Wachter H, Hentze M W. Iron regulates nitric oxide synthase activity by controlling nuclear transcription. J Exp Med 1994; 180: 969-76).

SUMMARY OF THE INVENTION

Thus, it is an object of the present invention to provide a cough depressant composition for angiotensin-converting enzyme inhibitor-induced cough.

In order to accomplish the object, the present invention provides a cough depressant composition containing iron.

DETAILED DESCRIPTION OF THE INVENTION

Figure 1:
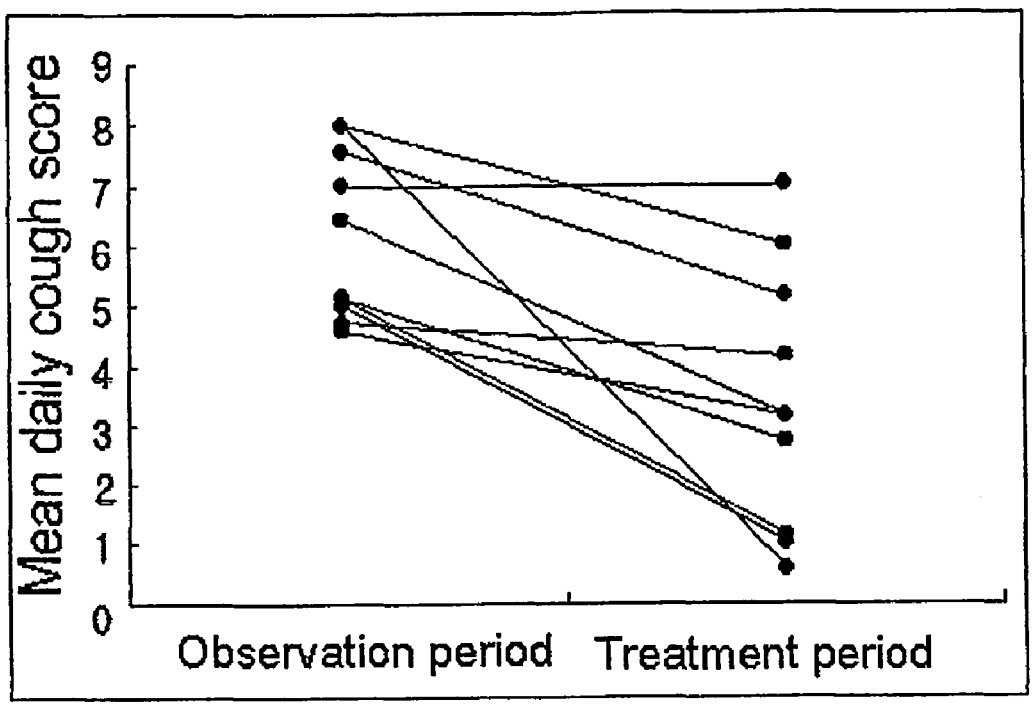
FIG. 1 is a graph showing the change in cough scores when taking ferrous sulphate, a dry cough depressant composition containing iron.

Hereinafter, the present invention will be explained in detail.

As a result of research to inhibit dry cough shown in patients who take angiotensin-converting enzyme inhibitors ('ACEIs'), the present inventors assumed nitrogen oxide induced by ACEIs to be a cause of the dry cough and completed the present invention by studying a method to inhibit generation of nitrogen oxide.

Nitric oxide is generated by nitric oxide synthase and is known to have correlation with an iron concentration in the body. The activity of the nitric oxide synthase is inhibited by increases of iron concentration in the body. Therefore, the present invention developed a cough depressant composition containing iron to reduce ACEI-induced dry cough.

The cough depressant composition containing iron for inhibiting ACEI-induced cough is preferably medicine comprising iron agent or iron. The iron is preferably $Fe^{2+}$ (ferrous) or $Fe^{3+}$ (ferric), and the medicine containing iron is preferably iron medicine prescribed for iron deficiency anemia or other iron deficient symptoms.

The research pertaining to the ACEI-induced cough depressant effect by the iron was carried out with nineteen patients taking ACEI. These subjects were patients who developed cough as a result of the side effect caused by taking ACEI. The experiment period was divided into the observation period and the treatment period. 10 of the patients took iron and 9 of the patients took placebo. As a result, 9 of the patients who had taken iron showed reduction in cough, but only one of the nine patients taking the placebo showed reduction in cough. Therefore, the cough depressant composition containing iron according to the present invention effectively decreases ACEI-induced cough.

various reasons. They include 6 men and 13 women, whose mean age was 59.9±12.2 years. The patients were divided into groups; the treatment group, which comprised 10 patients taking iron, and the control group, comprising 9 patients taking placebo. The characteristics of the patients are denoted in Table 1. All the patients gave informed consent, and the test was approved by the ethical committee of the Samsung Medical Center and Samsung Biomedical Research Center, Seoul, Korea.

TABLE 1

| Patient | Age | Gender | Diagnosis | ACEI | Other drug | Smoking | Group |
|---|---|---|---|---|---|---|---|
| 1 | 37 | M | Hypertension | Lisinopril | Atenolol | − | Iron intake |
| 2 | 57 | M | Aortic regurgitation | Enalapril | — | − | Iron intake |
| 3 | 59 | M | Hypertension | Enalapril | Diltiazem, Isorsobide, mononitrate | − | Iron intake |
| 4 | 36 | F | Mitral stenosis Aortic regurgitation | Fosinopril | Digoxin, Hydrochlorthiazide | − | Iron intake |
| 5 | 55 | F | Hypertension | Enalapril | Amlodipine | − | Iron intake |
| 6 | 59 | F | Hypertension | Cilazapril | Amlodipine | − | Iron intake |
| 7 | 70 | F | Left ventricle dysfunction | Captopril | — | − | Iron intake |
| 8 | 72 | F | Hypertension | Captopril | Atenolol | − | Iron intake |
| 9 | 73 | F | Left ventricle failure, Angina | Captopril | Isorsobide mononitrate, Nicorandil, Furosemie | − | Iron intake |
| 10 | 73 | F | Hypertension | Enalapril | Betaxolol | − | Iron intake |
| 11 | 44 | M | Aortic regurgitation | Enalapril | — | + | Placebo |
| 12 | 59 | M | Left ventricle dysfunction | Enalapril | Carvedilol | − | Placebo |
| 13 | 71 | M | Left ventricle dysfunction, Angina | Cilazapril | Betaxolol, Isorsobide mononitrate | + | Placebo |
| 14 | 43 | F | Left ventricle dysfunction | Enalapril | Betaxolol, Furosemide | − | Placebo |
| 15 | 61 | F | Aortic regurgitation | Captopril | — | − | Placebo |
| 16 | 62 | F | Hypertension | Enalapril | Atenolol, Amlodipine | − | Placebo |
| 17 | 64 | F | Left ventricle dysfunction | Fosinopril | Digoxin, Atenolol | − | Placebo |
| 18 | 71 | F | Old myocardinal infarction | Captopril | Metoprolol, Isorsobide mononitrate | − | Placebo |
| 19 | 72 | F | Left ventricle dysfunction, Angina | Captopril | Isorsobide mononitrate, Atenolol | − | placebo |

The cough depressant composition containing iron of the present invention can comprise only iron or further comprise other pharmaceutically acceptable medicine. The cough depressant composition further comprising other medicine preferably includes 0.01~100% by weight of iron. Also, the cough depressant composition can be administered alone or in combination with ACEI.

The cough depressant composition containing iron of the present invention for inhibiting cough caused by an ACEI can be formulated as any type comprising iron as an efficient ingredient. Preferably, the formulation is for oral or syringe application. The oral formulation is preferably tablets, capsules, soft capsules, fluid, granular type, pills, etc. The syringe formulation is preferably solution, suspension, emulsion, etc. The cough depressant containing iron of the present invention preferably comprises carrier excipients to manufacture into the above formulation. The carrier excipients can be starch, water, saline solution, ringer's solution and dextrose solution, etc. Appropriate agents known in the technical fields are disclosed in the document of Remington's Pharmaceutical Science (recent version)[Mack Publishing Company, Easton Pa.].

Hereinafter, preferable examples are presented for the sake of understanding. These examples, however, are provided to facilitate the understanding and the present invention is not limited to the following example.

EXAMPLE

The effect of the cough depressant containing iron of the present invention was tested. The cough depressant composition used in the test was ferrous sulphate. Anemia medicine sold as Feroba (trademark), whose ferrous sulphate was removed, was used as the placebo. The 19 tested patients had developed persistent dry cough while taking ACEI for 1. Observation Period ACEI-induced cough was defined as dry cough that occurred with ACEI use that subsided in seven days after discontinuation of the drug, and reappeared within 48 hours after the re-introduction of the drug and with no abnormality in the lungs and the bronchi.

19 patients completed a cough diary during a 2-week observation period while taking ACEI only. They were asked to fill in their cough severity daily according to the following scale; 0 indicates no cough, 1 indicates only a tickling sensation on the throat, 2 indicates mild cough that did not interfere with everyday life, 3 indicates moderate cough which was tolerable for sleep but severe enough to interrupt daily activities for some time, and 4 indicates severe cough which persisted and interfered with most of the daily activities or disturbed sleeping at night. Each day was divided into two 12-hour periods. The daytime period began at 8 A.M., and the nighttime period, vice versa. Patients recorded the cough score for each period.

2. Treatment Period

At the end of the observation period, blood samples were drawn from the patient for evaluation of hemoglobin level, hematocrit, iron concentration, total iron binding capacity ("TIBC"), and ferritin concentration. After sampling, they were randomized to either an iron taking group or placebo taking group. 256 mg of ferrous sulfate (of which 80 mg is ferrate) was daily administered to the iron taking group. During the four weeks of the treatment period, subjects were asked to fill in a cough diary in the identical way that they completed the diary in the observation period. After four weeks of the treatment period, blood sampling was repeated for the same evaluation (hemoglobin level, hematocrit, iron concentration, total iron binding capacity ("TIBC") and ferritin concentration) that was performed in the initiation of the treatment period.

3. Analysis

Cough scores from the last week of the observation period and the last week of the treatment period were compared and evaluated. The total sum of the cough scores were calculated from cough scores during the daytime and the nighttime recorded from the range of 0 to 4 for the last week of the observation period and the treatment period, and mean daily cough scores were calculated by dividing the total amount by days. Also, the cough score during the daytime and the nighttime was compared separately. The result was expressed as mean±standard deviation and analysis was performed using the SPSS software (SPSS Inc, II, USA). The two groups were compared using Wilcoxon's signed rank sum test. The following Table 2 shows the cough score during the observation and treatment period.

TABLE 2

| | | Degree of cough (score, mean standard deviation) | |
|---|---|---|---|
| Group | Period | Observation period | Treatment period |
| Iron taking group | Daily | 6.14 ± 1.41 | 3.39 ± 2.20 |
| | Daytime | 2.86 ± 0.86 | 1.51 ± 1.00 |
| | Nighttime | 3.29 ± 0.73 | 1.87 ± 1.24 |
| Control group | Daily | 5.14 ± 1.61 | 4.70 ± 2.44 |
| | Daytime | 2.37 ± 0.73 | 2.37 ± 1.23 |
| | Nighttime | 2.78 ± 0.97 | 2.33 ± 1.21 |

As can be seen in Table 2, the mean daily cough score in iron taking group was 6.14±1.41 at the last week of the observation period and 3.39±2.20 at the last week of the treatment period, showing a significant reduction of dry cough with iron supplementation. The reduction in cough scores was exhibited in both the daytime and nighttime period. No significant change in the mean daily cough scores was found in the placebo taking group (5.14±1.61 and 4.70±2.44, at the end of the observation and treatment period). Individual changes in the mean cough scores are shown in FIGS. 1 and 2.

FIG. 1 is a graph showing the change of cough scores when ferrous sulphate, which is the cough depressant composition containing iron. The cough score in the treatment period is significantly reduced. That is, 9 of 10 patients who took iron showed a decrease in the cough score and three patients showed an almost complete abolishment of cough in the iron taking group.

Figure 2:
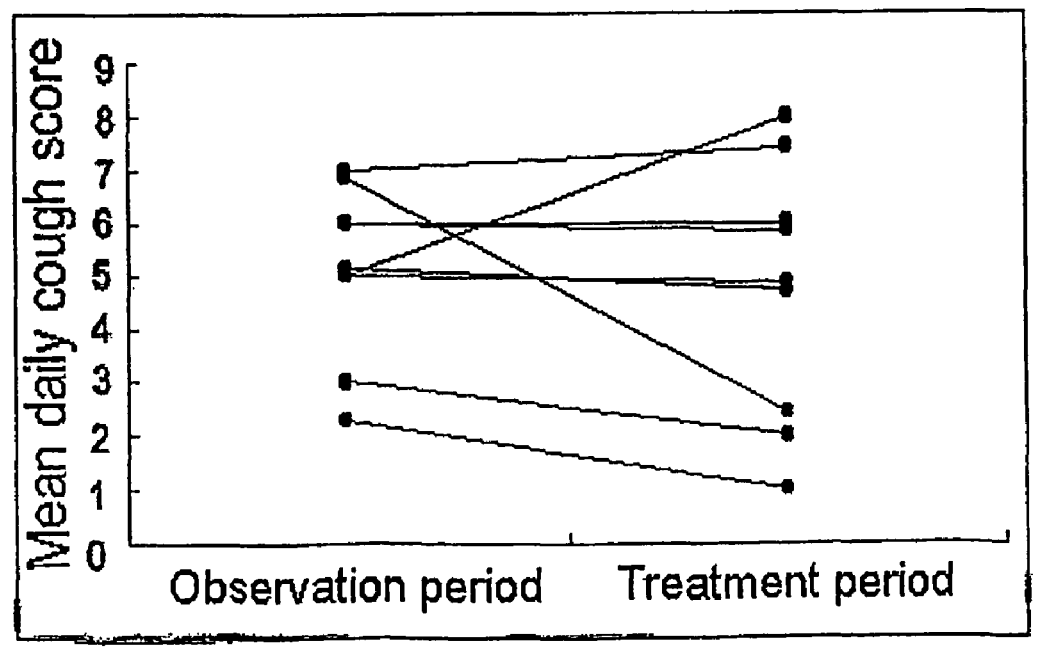
FIG. 2 is a graph showing the change in cough scores in subjects who took placebo as a control group.

FIG. 2 is a graph showing the change of cough scores when the control group has taken placebo. There was no significant reduction of cough scores in the placebo taking group and only one of the nine subjects showed improvement.

The hemoglobin level, hematocrit, iron concentration, TIBC and ferritin concentration in blood samples taken before the treatment period and after the treatment were compared. The result is shown in the following Table 3.

TABLE 3

| | Iron taking group | | Placebo taking group | |
|---|---|---|---|---|
| | Pretreatment | Posttreatment | Pretreatment | Posttreatment |
| Hemoglobin (mg/dL) | 13.43 ± 0.81 | 13.63 ± 0.60 | 13.45 ± 1.12 | 13.34 ± 1.39 |
| Hematocrit (%) | 39.58 ± 2.65 | 40.78 ± 2.51 | 40.31 ± 3.65 | 39.61 ± 3.92 |
| Iron (mg/dL) | 74.75 ± 10.53 | 83.75 ± 16.07 | 93.00 ± 48.70 | 97.16 ± 17.27 |
| TIBC (mg/dL) | 312.5 ± 28.1 | 320.3 ± 11.9 | 287.8 ± 39.7 | 287.8 ± 47.6 |
| Ferritin (mg/dL) | 68.15 ± 32.86 | 86.03 ± 25.78 | 102.47 ± 46.17 | 98.97 ± 41.58 |

As can be seen in Table 3, no significant difference was observed in hemoglobin, hematocrit, iron concentration, TIBC and ferritin concentration between the iron taking group and the placebo taking group. In the iron taking group, the mean ferritin level of 68.15±32.86 was increased to 86.03±25.78 mg/dL after the supply of iron. In the control group, the ferritin level decreased, but the difference did not reach a significant level.

As mentioned above, the dry cough depressant composition containing iron of the present invention prevents the side effect of angiotensin-converting enzyme inhibitor by reducing angiotensin-converting enzyme inhibitor induced cough, and reduces the troubles experienced by patients taking the angiotensin-converting enzyme inhibitor.

What is claimed is:

1. A method for inhibiting dry cough induced by angiotensin-converting enzyme inhibitors, the method comprising the step of orally administering iron as an active ingredient for inhibiting dry cough induced by angiotensin-converting enzyme inhibitors to a patient in need thereof, wherein the iron comprises ferrous sulphate.

2. The method according to claim 1, further comprising the step of administering an angiotensin-converting enzyme inhibitor.

3. A method for inhibiting dry cough induced by angiotensin-converting enzyme inhibitors, the method comprising the step of orally administering a composition comprising iron as an active ingredient for inhibiting dry cough induced by angiotensin-converting enzyme inhibitors to a patient in need, wherein the amount of iron in the composition is from 31.25 to 100 weight percent.

4. A method for inhibiting dry cough induced by angiotensin-converting enzyme inhibitors, the method comprising the step of orally administering iron as an active ingredient for inhibiting dry cough induced by angiotensin-converting enzyme inhibitors to a patient in need thereof, wherein the iron is formulated in a fluid form.

* * * * *